(12) United States Patent
Nuijten et al.

(10) Patent No.: US 7,045,122 B2
(45) Date of Patent: May 16, 2006

(54) SALMONELLA VACCINE

(75) Inventors: Petrus Johannes Maria Nuijten, Sambeek (NL); Maarten Hendrik Witvliet, Oostrum (NL)

(73) Assignee: Akzo Nobel N.V., Arnhem (NL)

( * ) Notice: Subject to any disclaimer, the term of this patent is extended or adjusted under 35 U.S.C. 154(b) by 26 days.

(21) Appl. No.: 10/432,102

(22) PCT Filed: Nov. 15, 2001

(86) PCT No.: PCT/EP01/13396

§ 371 (c)(1),
(2), (4) Date: May 16, 2003

(87) PCT Pub. No.: WO02/40046

PCT Pub. Date: May 23, 2002

(65) Prior Publication Data

US 2004/0052802 A1 Mar. 18, 2004

(30) Foreign Application Priority Data

Nov. 16, 2000 (EP) .................................. 00204022
Dec. 8, 2000 (EP) .................................. 00204387

(51) Int. Cl.
*A01N 63/00* (2006.01)
*A61K 39/00* (2006.01)
*A61K 39/02* (2006.01)
*A61K 39/112* (2006.01)

(52) U.S. Cl. ................ 424/93.1; 424/93.2; 424/184.1; 424/234.1; 424/235.1; 424/258.1

(58) Field of Classification Search ............. 424/184.1, 424/234.1, 235.1, 258.1
See application file for complete search history.

(56) References Cited

FOREIGN PATENT DOCUMENTS

| WO | 0 650 733 | 5/1995 |
| WO | 97 18837 | 5/1997 |
| WO | 98 56901 | 12/1998 |
| WO | WO 98/56901 | * 12/1998 |

OTHER PUBLICATIONS

Thomas E. Creighton, in his book, Proteins: Structures and Molecular Properties, 1984.*
Thomas E. Creighton, in his book "Protein Structure: A Practical Approach, 1989, pp. 184-186".*
Nosoh, Y. et al in "Protein Stability and Stabilization through Protein Engineering, 1991" (chapter 7, p. 197, second paragraph).*
Ferguson et al, (Mutation Research, 1987, 184 13-21).*
Buchmeier et al, (Molecular Microbiology, 1993, 7(6), 933-936).*
Mortelmans et al Journal of Bacteriology, 128, 271-282, 1976.*
Griffin et al, Vaccine, 1993, vol. 11, No. 4, p. 457-62.*
Griffin, Worlds Poult. Sci.J., 1991, vol. 47, No. 2, p. 129-40.*
Ferguson L R et al: "Frameshift Mutagenesis by Nitracrine Analogues in Wild-Type uvr-B pol-A and rec-A Strains of *Salmonella-typhimurium* With and Without Plasmid p-KM-101"; Mutations Research; vol. 184, No. 1, 1987, pp. 13-21.
Johnson B N et al: "Construction of *Salmonella* Strains with Both Antigen 04 of Gropu B and Antigen 09 of Group D"; Journal of Bacteriology, vol. 174, No. 6, 1992, pp. 1911-1915.
Buchmeier Nancy A et al: "Recombination-Deficient Mutants of *Salmonella typhimurium* are Avirulent and Sensitive to the Oxidative Burst of Macrophages."; Molecular Microbiology, vol. 7, No. 6, 1993, pp. 933-936.
Guerry, P. et al.: "Development and Characterization of recA Mutants of *Campylobacter jejuni* for Inclusion in Attenuated Vaccines"; Infection and Immunity; vol. 62, No. 2, Feb. 1994.

* cited by examiner

Primary Examiner—Lynette R. F. Smith
Assistant Examiner—Vanessa L. Ford
(74) *Attorney, Agent, or Firm*—Mark W. Milstead; David M. Gryte

(57) ABSTRACT

The present invention relates to live attenuated *Salmonella* strains comprising a first attenuating mutation, that are not capable of making functional RecA. The invention also relates to these bacteria for use in vaccines. Furthermore, the invention relates to vaccines based upon these bacteria, to the use of such bacteria in the manufacture of vaccines and to methods for the preparation of such vaccines.

9 Claims, No Drawings

SALMONELLA VACCINE

FIELD OF THE INVENTION

The present invention relates to an attenuated *Salmonella* strain comprising a first attenuating mutation, its use in vaccines, vaccines based upon this strain and methods for the preparation of such vaccines.

BACKGROUND OF THE INVENTION

Bacteria of the genus *Salmonella* are notorious for their pathogenicity in both man and animals. In the USA alone, on a yearly basis the number of humans suffering from *Salmonella* infections exceeds the two million cases. In most cases, the infection is caused by contaminated food. Well-known sources of infection are eggs (from both ducks and chickens), products containing eggs and not sufficiently heated poultry and pig meat. Especially in infants, young children, elderly people and immune compromised patients, the ability to cope with such infections is low. In these groups, the yearly death rate due to *Salmonella* infections is high. During the last few decades the more efficient large-scale animal husbandry has led to an enormous increase in animal density. As a result, an increase is seen of the number of animal infections and subsequently in human infections caused by infected food. It is clear that animals are the main source of *Salmonella* infection. This source is very difficult to control. First of all *Salmonella* infections in most cases cause no serious illness in healthy full-grown animals; these animals can carry the bacterium for a prolonged period. During that time they are shedding the bacterium in their dung. This makes it practically impossible to avoid infection in the more vulnerable young animals. Secondly, many *Salmonella* species colonise several different host species. Some of the *Salmonella* species cause primary infections in specific hosts, whereas other *Salmonella* species are not restrictive at all. As a primary infectans, *S. typhi* and *paratyphi* are frequently associated with infection in man. *S. dublin* is connected with cattle, *S. abortus-equi* causes abortion in horses. *S. abortus-ovi* causes abortion in sheep. *S. choleraesuis* is the cause of lethal diarrhoea in young pigs. *S. typhimurium* and *S. enteritidis* cause salmonellosis in humans, poultry, pigs, cattle and rodents, *S. arizonae* causes disease in turkeys, whereas *S. gallinarum* causes salmonellosis only in poultry.

It is clear that there is a need for good, safe and efficacious vaccines for combating the various *Salmonella* species. Currently, several live attenuated *Salmonella* vaccines are commercially available.

Many of the strains that are suitable for use in a live vaccine are attenuated to a level that makes them virtually non-virulent. Two striking examples of such non-virulent strains are the *Salmonella gallinarum* 9R strain and the *Salmonella typhimurium* SL3261 strain.

The *Salmonella gallinarum* 9R strain was described as long as 44 years ago by Smith (J. Hyg. Camb., 54:419–432 (1956)). This highly attenuated strain is known to have at least a mutation in a gene involved in the synthesis of the cell's O-polysaccharides, leading to a Smooth→Rough mutation. The 9R strain has been used as a Rough reference strain since then (see e.g. Cameron, C. M. et al., Onderstepoort J. Vet. Res. 39(3), 139–146 (1972)). This strain can be administered to chicken even in a dose of $10^9$ bacteria without causing the death of any chicken, whereas a dose comprising $10^3$ wild-type bacteria kills all animals.

The *Salmonella typhimurium* SL3261 strain has been described 19 years ago by Hoiseth, S. and Stocker, B. A. D. (Nature 291: 238–239(1981)) and is available from Deposit number SGSC 439, *Salmonella* Genetic Stock Centre, University of Calgary, Alberta, Canada T2N 1N4.

This strain is known to have a highly attenuating mutation in the aromatic pathway synthesis. This strain can be administered even in a $10^6$ bacteria dose to susceptible mice without causing the death of any animal, whereas the $LD_{50}$ of the parent strain for these mice is less then 20 bacteria.

Such *Salmonella* strains have since long been appreciated for their highly attenuated character. They are so severely attenuated that they are described in the literature as non-virulent. Therefore they have been the strains of choice for live attenuated *Salmonella* vaccines.

In principle, there is a clear relation between the level of virulence and the level of immunity induced. In general the strains with the highest virulence induce the highest levels of immunity: animals that survive infections with wild-type *Salmonella* strains often build up a long-lasting immunity. On the other hand, for use in vaccines those strains that induce no pathogenesis at all, the non-virulent strains, are the most desirable but such strains are often not capable of inducing a sufficiently high level of immunity. The non-virulent *Salmonella* strains described above are just about capable of triggering the immune system to a sufficient level.

A relevant disadvantage of all live attenuated vaccines is however, that in principle they can revert to a wild-type level of virulence through recombination of the mutated gene with DNA from bacteria that do carry non-mutated genes, such as e.g. wild-type field strains. Such a recombination event can take place in various ways, e.g. through transfection, transduction or transformation. Genes that are known to play a role in these recombination processes are known as rec-genes. One of the rec-genes of key importance is the recA-gene. This gene encodes an enzyme RecA that is involved in several steps of the recombination process. recA and many other rec-genes have been described i.a. by Lloyd. R. G. and Low, K. B. ("*Escherichia coli* and *Salmonella*", sec. ed., ASM Press, ISBN 1-55581-0-845, par. 119 page 2236–2255), by West, S. C. (Annu. Rev. Biochem. 61: 603–640 (1992), and by Kowalczykowski. S. C. et al (Microbiol Rev. 58: 401–465 (1994)).

At first sight it seems therefore tempting, when contemplating a safe live attenuated vaccine, to delete one of the rec-genes. Such a deletion severely impairs the ability of the bacterial DNA to recombine. Nevertheless, deletion of rec-genes is also known to cause severe attenuation of the bacterial strains from which it has been deleted. Deletion of e.g. the recA- or the recBC-genes in *Salmonella* makes the mutants sensitive to the oxidative burst of macrophages, which leads i.a. to significant in vivo growth suppression. This has been demonstrated for *Salmonella*, e.g. by Buchmeier, N. A. et al., (Mol. Microbiol, 7:933–936 (1993)) and equally convincing for other bacterial genera as distantly related to *Salmonella* as e.g. *Vibrio cholerae* (Ketley et al., Infect. and Immun. 58: 1481–1484 (1990)).

Thus, where deletion of a rec-gene might be an advantage for virulent strains, it certainly would be assumed to be a disadvantage for non-virulent strains, such as the *Salmonella gallinarum* 9R strain and the *Salmonella typhimurium* SL3261 strain. These strains, known to be already highly impaired, could not be expected to trigger any immunological response at all after removal of rec-genes. This may explain why no attempts were made to delete Rec-genes from such already highly attenuated, non-virulent strains as *S. gallinarum* 9R and *S. typhimurium* SL3261, in spite of their long history.

DETAILED DESCRIPTION OF THE INVENTION

It is an objective of the present invention to provide live attenuated *Salmonella* vaccines that are both safe and efficacious. It was surprisingly found now, that deletion of the virulence factor RecA does not further impair the ability of already attenuated *Salmonella* strains to adequately trigger the immune system in comparison to their RecA-positive counterparts.

Therefore, one embodiment of the invention provides attenuated *Salmonella* strains that already comprise a first attenuating mutation and that have as a characteristic feature that they additionally comprise a mutation that prohibits these strains from making a functional RecA protein.

Attenuated strains that already comprise a first attenuating mutation are understood to be strains that have a sufficiently attenuated character to be used as a basis for live attenuated vaccines due to an already existing attenuation. The nature of that first attenuation is not relevant. It can be any attenuating mutation or combination of two or more mutations having a sufficiently attenuated character to make the bacterium useful as a basis for a live attenuated vaccine. Merely as an example, it can e.g. be a Rough-mutation, a mutation in the histidin- or purin synthesis pathway or a mutation in the aromatic amino acid biosynthesis pathway. Also mutations in the cra-gene, and crp/cya-mutations, known in the art are suitable mutations. Also, known *Salmonella* vaccine strains are very suitable as a basis for the production of a RecA negative bacterium according to the present invention.

Strains not capable of making functional RecA are understood to be strains that either make no RecA enzyme at all, or to a level that is essentially insufficient to lead to RecA-driven recombination events. This incapability to make RecA can i.a. be the result of mutation or deletion of a part of, or of the whole recA gene, the recA promotor or a gene involved in recA synthesis.

In a preferred form of this embodiment, *Salmonella* strains according to the invention belong to the species *Salmonella gallinarum* or *Salmonella typhimurium*.

In a more preferred form of this embodiment the *Salmonella gallinarum* strain is *Salmonella gallinarum* 9R.

An even more preferred form of this embodiment relates to the strain *Salmonella gallinarum* 9R-RecA of which a sample is deposited with the Centraalbureau voor Schimmelcultures, Oosterstraat 1, 3742 SK Baarn, The Netherlands under deposit number CBS 108964.

In another more preferred form of this embodiment the *Salmonella typhimurium* strains is *Salmonella typhimurium* SL3261.

One possible way of making the recA gene or any of the other known genes involved in RecA-biosynthesis non-functional is by means of classical methods such as the treatment of wild-type bacteria with mutagenic agents such as base analogues, treatment with ultraviolet light or temperature treatment (Anderson, P. 1995. Mutagenesis, p 31–58 in Methods in Cell Biology 48. H. F. Epstein and D. C. Shakes (Eds)). Other methods for making RecA-negative mutants of various bacteria of which the wild type is RecA-positive, have been described i.a. by Liu, S. L. et al. (Infect. Immun. 1988 Aug; 56(8): 1967–73), Haas, R. et al.,
(Mol. Microbiol. 1993 May; 8(4): 753–60) and Graf, J. et al. (J. Bacteriol. 1994 November; 176(22): 6986–91).

RecA-negative mutants can easily be selected because of their much higher sensitivity for U.V.-radiation. A classical way of detecting the mutants amidst non-mutated bacteria is by replica-plating. This technique starts with an agar plate covered with bacterial colonies that have been subjected to a mutagenic treatment. A replica of this plate is made onto a second agar plate. This plate is then subjected to a high does of U.V.-radiation. Those colonies that do no longer grow after radiation treatment are colonies that have a mutation in a rec gene. Their live replica colonies on the original plate can then be selected and grown for e.g. vaccine purposes.

The exact nature of the mutation caused by classical mutation techniques is usually unknown. This can e.g. be a point mutation which may, although this is unlikely to happen, eventually revert to wild-type. Therefore transposon mutagenesis is a good alternative. Mutation by transposon mutagenesis is also a mutagenesis-technique well-known in the art. This is a mutation accomplished at a localised site in the chromosome. A possibility to introduce a mutation at a predetermined site, rather deliberately than randomly, is offered by recombinant DNA-technology. Such a mutation may be an insertion, a deletion, a replacement of one nucleotide by another one or a combination thereof, with the only proviso that the mutated gene no longer encodes functional RecA. Such a mutation can e.g. be made by deletion of a number of base pairs. Even very small deletions such as stretches of 10 base pairs can already cause the recA-gene to encode a non-functional RecA. Even the deletion of one single base pair may already lead to a non-functional RecA, since as a result of such a mutation, the other base pairs are no longer in the correct reading frame. Each deletion or insertion of a number of base pairs indivisible by three causes such a frame shift. More preferably, a longer stretch is removed e.g. 100 base pairs. Even more preferably, the whole recA-gene is deleted.

All recombinant DNA techniques for the construction of recA-negative mutants are well-known standard techniques. They relate to cloning of the recA-gene, modification of the gene sequence by site-directed mutagenesis, restriction enzyme digestion followed by re-ligation or PCR-approaches and to subsequent replacement of the wild type recA gene with the mutant gene (allelic exchange or allelic replacement). Standard recombinant DNA techniques such as cloning the recA gene in a plasmid, digestion of the gene with a restriction enzyme, followed by endonuclease treatment, re-ligation and homologous recombination in the host strain, are all known in the art and described i.a. in Maniatis/Sambrook (Sambrook, J. et al. Molecular cloning: a laboratory manual. ISBN 0-87969-309-6). Site-directed mutations can e.g. be made by means of in vitro site directed mutagenesis using the Transformer® kit sold by Clontech. PCR-techniques are extensively described in (Dieffenbach & Dreksler; PCR primers, a laboratory manual. ISBN 0-87969-447-5 (1995)).

Given the large amount of vaccines given nowadays to both pets and farm animals, it is clear that combined administration of several vaccines would be desirable, if only for reasons of decreased vaccination costs. It is therefore very attractive to use live attenuated bacteria as a recombinant carrier for heterologous genes, encoding antigens selected from other pathogenic micro-organisms or viruses. Administration of such a recombinant carrier has the advantage that immunity is induced against two or more diseases at the same time. Live attenuated bacteria for use in a vaccine according to the present invention provide very suitable carriers for heterologous genes. In principle such heterologous genes can be inserted in the bacterial genome at any non-essential site.

Therefore, a still even more preferred form of this embodiment relates to bacteria according to the invention in which a heterologous gene is inserted. Such a heterologous gene can, as mentioned above, e.g. be a gene encoding an antigen selected from other pathogenic micro-organisms or viruses. Such genes can e.g. be derived from pathogenic herpesviruses (e.g. the genes encoding the structural proteins of herpesviruses), Retroviruses (e.g. the gp160 envelope protein), adenoviruses and the like. Also a heterologous gene can be obtained from pathogenic bacteria. As an example, genes encoding bacterial toxins such as *Actinobacillus pleuropneumoniae* toxins, *Clostridium* toxins, outer membrane proteins and the like are very suitable bacterial heterologous genes. Further, heterologous genes from various parasites, such as e.g. *Eimeria* are very attractive candidates for cloning in a live attenuated *Salmonella* vector according to the invention. Another possibility is to insert a gene encoding a protein involved in triggering the immune system, such as an interleukin, Tumor Necrosis Factor or an interferon, or another gene involved in immune-regulation.

In a most preferred form of this embodiment, the heterologous gene encodes an antigen of a micro-organism or virus that is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitisvirus, *Eimeria* species, *Pasteurella multocida, Mycoplasma synoviae, Salmonella* species, *Ornithobacterium rhinotracheale* and *E. coli*.

The use of the recA gene as an insertion site has the advantage that there is no need to find a new insertion site for the heterologous gene and at the same time the recA gene is inactivated and the newly introduced heterologous gene can be expressed (in concert with the homologous bacterial genes). The construction of such recombinant carriers can be done routinely, using standard molecular biology techniques such as allelic exchange.

Thus, in a preferred form of this embodiment the heterologous gene is inserted in the recA gene. The heterologous gene can be inserted somewhere in the recA gene or it can be inserted at the site of the recA gene while this gene has been partially or completely deleted.

Another embodiment of the invention relates to vaccines for combating *Salmonella* infection that comprise an attenuated *Salmonella* strain according to the invention and a pharmaceutically acceptable carrier. A pharmaceutically acceptable carrier may be as simple as water, but it may e.g. also comprise culture fluid in which the bacteria were cultured. Another suitable carrier is e.g. a solution of physiological salt concentration.

The useful dosage to be administered will vary depending on the age, weight and animal vaccinated, the mode and route of administration and the type of pathogen against which vaccination is sought. The vaccine may comprise any dose of bacteria, sufficient to evoke an immune response. Doses ranging between $10^3$ and $10^{10}$ bacteria are e.g. very suitable doses. Doses between $10^6$ and $10^9$ bacteria are even more preferred.

Optionally, one or more compounds having adjuvant activity may be added to the vaccine. Adjuvants are non-specific stimulators of the immune system. They enhance the immune response of the host to the vaccine. Examples of adjuvants known in the art are Freunds Complete and Incomplete adjuvant, vitamin E, non-ionic block polymers, muramyldipeptides, ISCOMs (immune stimulating complexes, cf. for instance European Patent EP 109942), Saponins, mineral oil, vegetable oil, and Carbopol. Adjuvants, specially suitable for mucosal application are e.g. the *E. coli* heat-labile toxin (LT) or *Cholera* toxin (CT). Other suitable adjuvants are for example aluminium hydroxide, aluminium phosphate or aluminium oxide, oil-emulsions (e.g. of Bayol F $^{(R)}$ or Marcol 52 $^{(R)}$, saponins or vitamin-E solubilisate.

Therefore, in a preferred form, the vaccines according to the present invention comprise an adjuvant.

Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer). Especially when such stabilisers are added to the vaccine, the vaccine is very suitable for freeze-drying or spray-drying.

Therefore, in a more preferred form, the vaccine is in a freeze-dried or spray-dried form.

For administration to animals or humans, the vaccine according to the present invention can be given inter alia intranasally, by spraying, intradermally, subcutaneously, orally, by aerosol or intramuscularly. Preferred methods for reason of convenience are administration by spraying, intranasal administration and oral administration. For application to poultry, wing-web and eye-drop administration are additionally suitable.

Still another embodiment of the invention relates to attenuated *Salmonella* strains according to the invention for use in a vaccine.

A further embodiment of the invention relates to attenuated *Salmonella* strains according to the invention for use in the manufacture of a vaccine for combating *Salmonella* infection.

The invention also relates to methods for the preparation of a vaccine according to the invention. Such methods comprise the admixing of attenuated *Salmonella* bacteria according to the invention or antigenic material thereof and a pharmaceutically acceptable carrier.

DEPOSIT OF BIOLOGICAL MATERIAL

Attenuated strain 9R ace was deposited on Sep. 21, 2000 under the terms of the Budapest Treaty at the Centraalbureau voor Schimmelcultures, Oosterstraat 1 P.O. Box 273, 3740 AG BAARN, The Netherlands, and has been assigned Accession No. CBS 108964. Pursuant to 37 C.F.R. §1.808, the biological material deposited is made under two conditions. First, access to the deposit will be made available during pendency of the patent application making reference to the deposit to one determined by the Commissioner to be entitled thereto under 37 C.F.R. §1.14 and 35 U.S.C. §122; and secondly with one exception, that restrictions imposed by the depositor on the availability to the public of the deposited material be irrevocably removed upon the granting of the patent.

EXAMPLE 1

Construction of a recA Mutant of *S. Gallinarum* 9R and *S. Typhimurium* SL3261.

The complete recA locus and flanking regions, approximately 4 kb, of *S. gallinarum* 9R and *S. typhimurium* SL3261 was cloned and sequenced. (Methods used for cloning were standard methods as described by Maniatis/Sambrook (referenced above), RecA genes were detected as described by Lloyd, West and Kowalczykowski (referenced above), methods for sequencing are standard methods well-known in the art). Based on this sequence, the two flanking regions of the recA gene were amplified by PCR; 1 kb upstream recA and 1 kb downstream of recA. These two PCR fragments were connected to each other by overlap-extension PCR in such a way that the orientation of the fragments was correct. This PCR fragment, representing the recA locus with a deletion of most of the recA gene, was cloned into a *Salmonella* suicide vector pLD55 (resistant to ampicillin and tetracycline) in *Escherichia coli* S17.1 lambda-pir. This strain was used for allelic exchange to make a clean, marker-free recA mutant strain of *S. gallinarum* 9R and *S. typhimurium* SL3261, as described below.

By means of conjugation the recA deletion construct in pLD55 was transferred from *E. coli* into *S. gallinarum* 9R and *S. typhimurium* SL3261. Since this plasmid does not replicate in *Salmonella*, ampicillin resistant *S. gallinarum* 9R or *S. typhimurium* SL3261 colonies had the deletion construct integrated into their chromosome through homologous recombination at the recA locus. This was checked by PCR using different primer sets. In a second, spontaneous, intrachromosomal recombination step between recA DNA regions, pLD55 and flanking DNA are excised which lead to ampicillin and tetracycline sensitive colonies and at the same time the formation of i) a wild type recA locus or ii) a mutated recA locus containing the deletion as described above. Several of the ampicillin and tetracycline sensitive colonies were analyzed for their recA locus by means of PCR: the wild type recA locus gave a fragment of 1.4 kb and the deleted recA locus a fragment of 0.4 kb. For *Salmonella gallinarum* two out of 16 colonies showed the deleted recA locus and were confirmed to be recA mutants by sequence analysis of the recA PCR fragment and by their enhanced sensitivity to U.V. irradiation.

EXAMPLE 2

Vaccination Test

The efficacy against *S. enteritidis* of the 9R parent strain and the 9R recA mutant CBS 108964 was tested in a challenge experiment in laying-type chickens. Three groups of 15 previously unvaccinated chickens were used. One group was vaccinated intramuscularly with the 9R strain ($1.3\times10^7$ CFU/dose), one group was vaccinated with the recA mutant ($8.4\times10^6$ CFU/dose) and the third group was used as control. All chickens were challenge infected with a naladixic acid resistant *S. enteritidis* PT4 strain at 10 weeks of age ($1.0\times10^8$ CFU) via the oral route.

Two weeks after challenge, all chickens were necropsied and spleens, cloacal swabs and the caecum contents were cultured for the challenge strain. Direct inoculation on Brilliant Green Agar plates containing naladixic acid (BGA) and plating after enrichment in buffered peptone water containing naladixic acid was performed. Identity of *S. enteritidis* isolates was confirmed by agglutination with flagellum specific antiserum.

Animals

Commercial layers, 6 weeks of age were obtained from a *Salmonella* free flock.

Results

As shown in table 1, *S. enteritidis* colonisation rates of spleen and cloaca were highly reduced in both the 9R and the 9RrecA groups when compared to unvaccinated controls. Therefore it can be concluded that the efficacy of vaccines based upon both 9R and the 9RrecA is fully comparable.

TABLE 1

| | *S. enteritidis* positive | | |
|---|---|---|---|
| Group | 9R | 9RrecA | Control |
| Spleen | $1/15^a$ | $2/15^a$ | $11/15^b$ |
| Cloaca | $0/15^a$ | $0/15^a$ | $9/15^b$ |
| Caecum | $2/15^{a,c}$ | $0/15^{a,b}$ | $5/15^c$ |

Groups with different superscripts in a row differ significantly ($p < 0.05$, Fisher exact test)

We claim:

1. An attenuated *Salmonella* strain, wherein the strain:
comprises a first attenuating mutation decreasing the $LD_{50}$ of said strain at least 50,000 times when compared to wild-type strain,
comprises a mutation that prohibits the strain from making a functional RecA protein, and
is a *Salmonella gallinarum* 9R strain.

2. An attenuated *Salmonella* strain, wherein the strain is a *Salmonella gallinarum* 9R-RecA strain of which a sample is deposited with the Centraalbureau voor Schimmelcultures under deposit number CBS 108964.

3. An attenuated *Salmonella* strain, wherein the strain:
comprises a first attenuating mutation decreasing the $LD_{50}$ of said strain at least 50,000 times when compared to wild-type strain,
comprises a mutation that prohibits the strain from making a functional RecA protein, and
is a *Salmonella typhimurium*SL3261 strain.

4. A vaccine for combating *Salmonella* infection, comprising:
an attenuated *Salmonella* strain according to claim 1, and a pharmaceutically acceptable carrier.

5. A vaccine for combating *Salmonella* infection, comprising:
an attenuated *Salmonella* strain according to claim 2, and a pharmaceutically acceptable carrier.

6. A vaccine for combating *Salmonella* infection, comprising:
an attenuated *Salmonella* strain according to claim 3, and a pharmaceutically acceptable carrier.

7. A method for the preparation of a vaccine for combating *Salmonella* infection, comprising admixing:
an attenuated *Salmonella* strain according to claim 1, and a pharmaceutically acceptable carrier.

8. A method for the preparation of a vaccine for combating *Salmonella* infection, comprising admixing:
an attenuated *Salmonella* strain according to claim 2, and a pharmaceutically acceptable carrier.

9. A method for the preparation of a vaccine for combating *Salmonella* infection, comprising admixing:
an attenuated *Salmonella* strain according to claim 3, and a pharmaceutically acceptable carrier.

* * * * *